US012662302B2

(12) United States Patent
Howell

(10) Patent No.: US 12,662,302 B2
(45) Date of Patent: Jun. 23, 2026

(54) MACHINE FOR MAKING CUSTOM DECORATIVE AIR TREATMENT ART

(71) Applicant: Kevin Laron Howell, Deltona, FL (US)

(72) Inventor: Kevin Laron Howell, Deltona, FL (US)

( * ) Notice: Subject to any disclaimer, the term of this patent is extended or adjusted under 35 U.S.C. 154(b) by 24 days.

(21) Appl. No.: 17/877,828

(22) Filed: Jul. 29, 2022

(65) Prior Publication Data

US 2023/0227240 A1 Jul. 20, 2023

Related U.S. Application Data

(60) Provisional application No. 63/227,962, filed on Jul. 30, 2021.

(51) Int. Cl.
| | |
|---|---|
| *B65D 83/26* | (2006.01) |
| *A61L 9/14* | (2006.01) |
| *B65D 83/30* | (2025.01) |
| *B65D 83/303* | (2025.01) |
| *B65D 83/38* | (2025.01) |
| *B65D 83/384* | (2025.01) |

(52) U.S. Cl.
CPC .............. *B65D 83/384* (2013.01); *A61L 9/14* (2013.01); *B65D 83/262* (2013.01); *B65D 83/267* (2013.01); *B65D 83/303* (2013.01); *A61L 2209/111* (2013.01); *A61L 2209/134* (2013.01); *A61L 2209/15* (2013.01)

(58) Field of Classification Search
CPC .. B65D 83/384; B65D 83/262; B65D 83/267; B65D 83/303; A61L 9/14; A61L 2209/111; A61L 2209/134; A61L 2209/15
See application file for complete search history.

(56) References Cited

U.S. PATENT DOCUMENTS

| | | | | | |
|---|---|---|---|---|---|
| 3,865,275 | A | * | 2/1975 | De Nunzio | .......... B65D 83/262 |
| | | | | | 222/639 |
| 4,570,824 | A | * | 2/1986 | Bolling | ................ B65D 83/267 |
| | | | | | 239/274 |
| 7,222,760 | B1 | * | 5/2007 | Tsay | ..................... B65D 83/262 |
| | | | | | 239/70 |
| 8,573,447 | B2 | * | 11/2013 | Muderlak | ............ B65D 83/262 |
| | | | | | 222/325 |
| 2010/0140298 | A1 | * | 6/2010 | Anderson | ................. A61L 9/12 |
| | | | | | 222/183 |
| 2011/0226805 | A1 | * | 9/2011 | Muderlak | ............ B65D 83/262 |
| | | | | | 222/23 |
| 2015/0307261 | A1 | * | 10/2015 | Chang | ................... B65D 83/262 |
| | | | | | 74/25 |
| 2015/0314032 | A1 | * | 11/2015 | Green | ................... B65D 83/388 |
| | | | | | 222/173 |
| 2015/0328356 | A1 | * | 11/2015 | Howell | ................ B65D 83/262 |
| | | | | | 222/61 |

* cited by examiner

*Primary Examiner* — Frederick C Nicolas

(57) ABSTRACT

The present invention relates to a customizable decorative air treatment machine. The machine provides a base structure that supports a variety of custom-made decorative housings, allowing users to easily replace and personalize the appearance of the device. The housing can be made from materials such as ceramics, wood, glass, metals, and various plastic resins, and can be decorated using techniques like painting, ceramic glazing, and other artistic methods. The customizable housing sits on a base and integrates seamlessly with the functional air treatment components, offering both aesthetic and practical benefits.

1 Claim, 13 Drawing Sheets

9

6

6

6

3

16

MACHINE FOR MAKING CUSTOM DECORATIVE AIR TREATMENT ART

FIELD OF THE INVENTION

The present invention relates to a novel automated air treatment machine which provides support for a custom-made decorative housing.

BACKGROUND

Current devices for treating the air, (i.e., automated air fresheners; sprays that provide respiratory support; and sprays formulated to reduce airborne biological pollutants such as pollen, viruses, and fungi), are not designed in a way that individuals can use the devices as platforms to support their own custom fabricated housings which can be made from a wide range of materials such as ceramics, wood, glass, metals, and various resins.

The current invention builds upon the prior art disclosed in US 2015/0328356 A1, which describes an automatic air freshener designed to appear like a spouting or spitting cetacean. US 2015/0328356 A1 includes a manufactured cetacean sculpture or an optional spherical housing with cetacean figurines attached, and the inner working parts such as a bracket holding an aerosol spray can, a motor, gears, a motor controller, batteries, and a tube. The working parts provide mechanisms for the cetacean to expel air freshener through its blowhole or mouth via a tube.

In contrast, the current invention embodies the components that enable craftspeople to create housings for air treatment devices (not exclusively intended to be used solely for air freshening as in US 2015/0328356 A1) that are uniquely expressive of the artist's individualistic creativity.

COMPREHENSIVE BACKGROUND OF THE INVENTION

The present invention relates to an air treatment machine that enhances both the aesthetic appeal and operational functionality of air treatment devices. While air treatment machines have been designed for various applications, including air sanitation and purification, odor neutralization, and environmental fragrance enhancement, many existing designs suffer from mechanical, structural, and functional limitations. The current invention addresses these issues with significant improvements over prior art, including Howell (US20150328356A1), which was authored by the present inventor.

In Howell (US20150328356A1), the prior design relied on a theoretical configuration that included a rocker arm gear assembly and a telescopic sliding mechanism with two latches to secure the aerosol spray can. While conceptually sound, this design was found to be nonfunctional during prototype testing. Specifically:

The rocker arm gear assembly failed to deliver sufficient force to reliably actuate the aerosol spray can nozzle. This rendered the system ineffective for its intended purpose.

The telescopic sliding mechanism, which connected the inner and outer half-cylinders of the prior art's major connector, was rendered inconvenient and unnecessary due to the one-piece circular design of the current invention's major connector. The prior art relied on:

1. A horizontal latch attached to the inner half-cylinder to secure the spray can horizontally across its center.
2. A bottom latch at the base of the outer half-cylinder to keep the inner half-cylinder in place during actuation.

However, the bottom latch failed to hold the spray can securely when exposed to downward forces during nozzle engagement. This resulted in mechanical instability and failure.

The prior art lacked a spring-and-pin assembly or a scotch yoke mechanism. These components were not part of the theoretical design, which relied solely on the rocker arm gear assembly to actuate the spray can nozzle.

To address these shortcomings, the present invention introduces the following key innovations:

Screw Cap Mechanism:
1. The screw cap replaces the ineffective bottom latch and eliminates the need for a telescopic sliding mechanism.
2. By securing the aerosol spray can directly to the major connector, the screw cap provides superior stability and ensures reliable actuation of the spray nozzle.

Full 360-Degree Major Connector:
1. Unlike the prior art's half-cylinder design with a telescopic sliding mechanism, the present invention employs a full 360-degree circular major connector with a threaded bottom.
2. This design allows the aerosol spray can to be inserted vertically through the bottom and securely retained by the screw cap, eliminating the need for a horizontal latch to hold the spray can in place.

Modified Scotch Yoke Mechanism:
1. The rocker arm gear assembly of the prior art is replaced with a modified scotch yoke mechanism, which converts rotary motion into linear motion.
2. This innovation delivers precise downward force to actuate the aerosol spray can nozzle, ensuring reliable operation.

Customizable Decorative Housing:
1. The present invention includes a decorative housing that is customizable and can be made by the end user.
2. This housing can be fabricated from various materials, such as glass, ceramic, wood, metal, or resins.
3. Designed to rest unattached on the base, the housing is easily removable, allowing users to personalize their air treatment machines without compromising functionality.
4. Unlike Howell (US20150328356A1), which allowed only manufacturer-customized housings, the present invention enables full artistic flexibility by the user.

By addressing the deficiencies of the prior art and introducing these novel features, the present invention provides a practical and reliable solution for air treatment applications while offering aesthetic versatility and user customization.

DESCRIPTION OF THE INVENTION

The Machine for Making Custom Decorative Air Treatment Art embodies the components that enable a person to fit a custom-made housing over the assembly of the machine's parts. Central to the machine's design is a base that supports the custom-made decorative housing along with supporting the machines working parts. The base will be round, oval, or of polygonal geometry. The end user will need to form the bottom of his or her housing to interface with the base for proper fit.

The novelty of the present invention, as disclosed in US 2023/0227240 A1 compared to US 2015/0328356 A1, lies in its unique ability to support customizable decorative housings. Unlike the cetacean-specific design in US 2015/0328356 A1, the current invention allows users to create and attach various custom housings made from different materials such as ceramics, wood, glass, metals, and resins to its base. Furthermore, the invention incorporates a modified scotch yoke mechanism which converts rotational motor motion into linear motion. Whereas in US 2015/0328356 A1 uses a set of gears and a rocker arm type lever gear to depress the nozzle of an aerosol can. The base, upon which a decorative housing rests in US 2023/0227240 A1, enables versatility and adaptability to different artistic expressions and decorative housing designs.

SUMMARY OF THE INVENTION

The present invention relates to an automated air treatment machine that supports customizable decorative housings.

Current devices for treating the air, such as automated air fresheners, do not allow individuals to use these devices as platforms for their custom fabricated housings, which can be made from materials such as ceramics, wood, glass, metals, and various resins. This invention includes components that enable craftspeople to create housings for air treatment devices, allowing unique artistic expression.

The Machine for Making Custom Decorative Air Treatment Art includes components enabling users to fit custom-made housings over the machine's parts. The design features a base supporting the decorative housing along with mechanical and electrical components. The base is round, oval, or polygonal geometry. Users can modify their housings to interface properly with the base.

The invention provides an aromatic spray mist for air treatment using a chemical mixture and or natural oils. The base supports a custom decorative housing, which can be made or purchased by the consumer. Common materials for the housing include ceramics, wood, glass, metals, and various resins. A ready-made ceramic housing is available in a kit, allowing customization through ceramic glazing, painting, or other forms of decorating.

The structural parts of the air treatment machine include a base, a major connector, a screw cap, and a motor mount. The working and electronic parts include a dc motor, a modified scotch yoke, a circular spindle, circuit boards, batteries, an instant spray button, a mode selection switch, a motion sensor, a remote control, and an on/off switch.

The major connector assembly holds an aerosol spray can. The motor applies rotational torque to the "modified scotch yoke" via an intermediary circular spindle attached to the motor's shaft, providing downward force to activate the aerosol can nozzle from which a vertical spray mist is ejected.

The device can direct the spray via a tube with a spray nozzle fixed to the tube's end, connected at the base of the "modified scotch yoke" which interfaces with and actuates the aerosol spray can nozzle. This modification allows for a spray mist that can be directed in any direction allowing for the creation of various decorative housings, creating diverse subject matter.

BRIEF DESCRIPTION OF THE DRAWINGS

FIG. 2 also provides the isometric view of the "modified scotch yoke mount/motor mount", detail 6.

DETAILED DESCRIPTION

Figure 8:
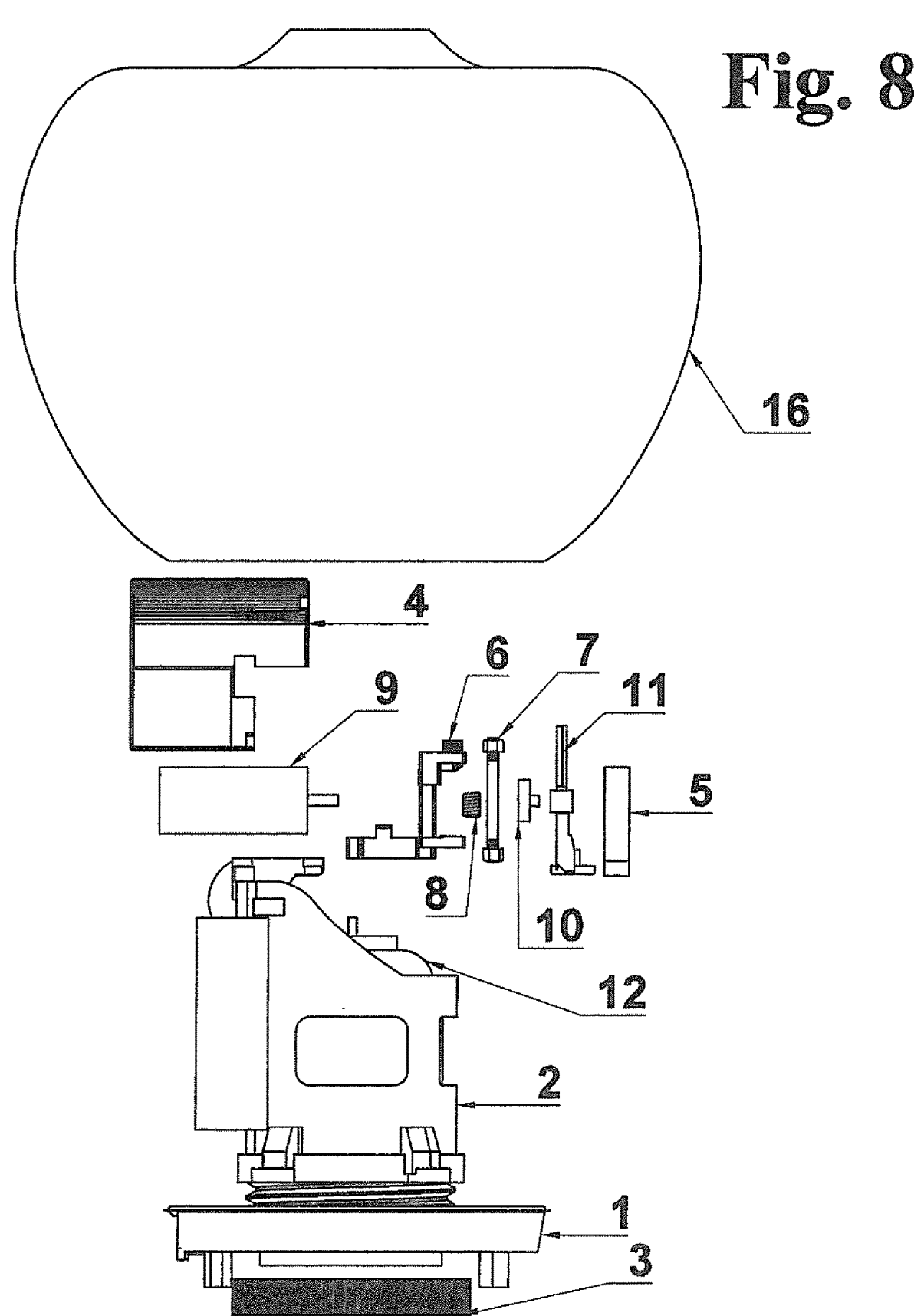
FIG. 8 is an exploded side view of the invention. Detail 10 is the scotch yoke spindle which is attached to the DC motor shaft. The spindle, detail 10, has a small, raised round cylinder near its peripheral border on its scotch yoke, detail 1, facing surface. The spindle's cylinder fits into the horizontal oval slot of the modified scotch yoke detail 11, FIG. 3.
Figure 9:
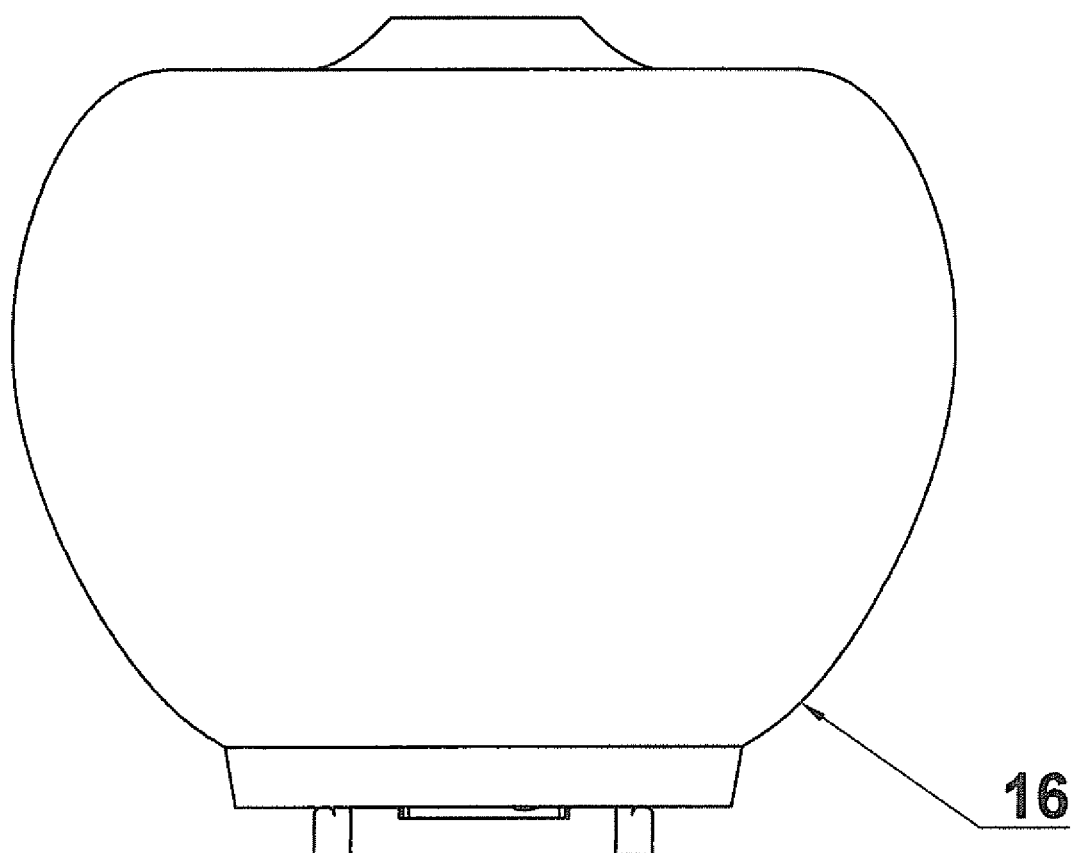
FIG. 9 is a rendering of the air treatment machine with an example of a custom decorative housing, detail 16, which fits over the working parts and rests on the base detail 1 FIGS. 1, 4, 6, and 8.

The invention is an air treatment device that has a base which holds and supports a custom decorative outer housing. The invention consists of the following embodiments with reference to FIGS. 1 to 13. FIG. 8 detail 16 is an example of a housing that can be custom made by the end user to fit over the air treatment machine to rest on the base, detail 1, FIGS. 1, 4, 6, 8, 12, and 13.

Figure 1:
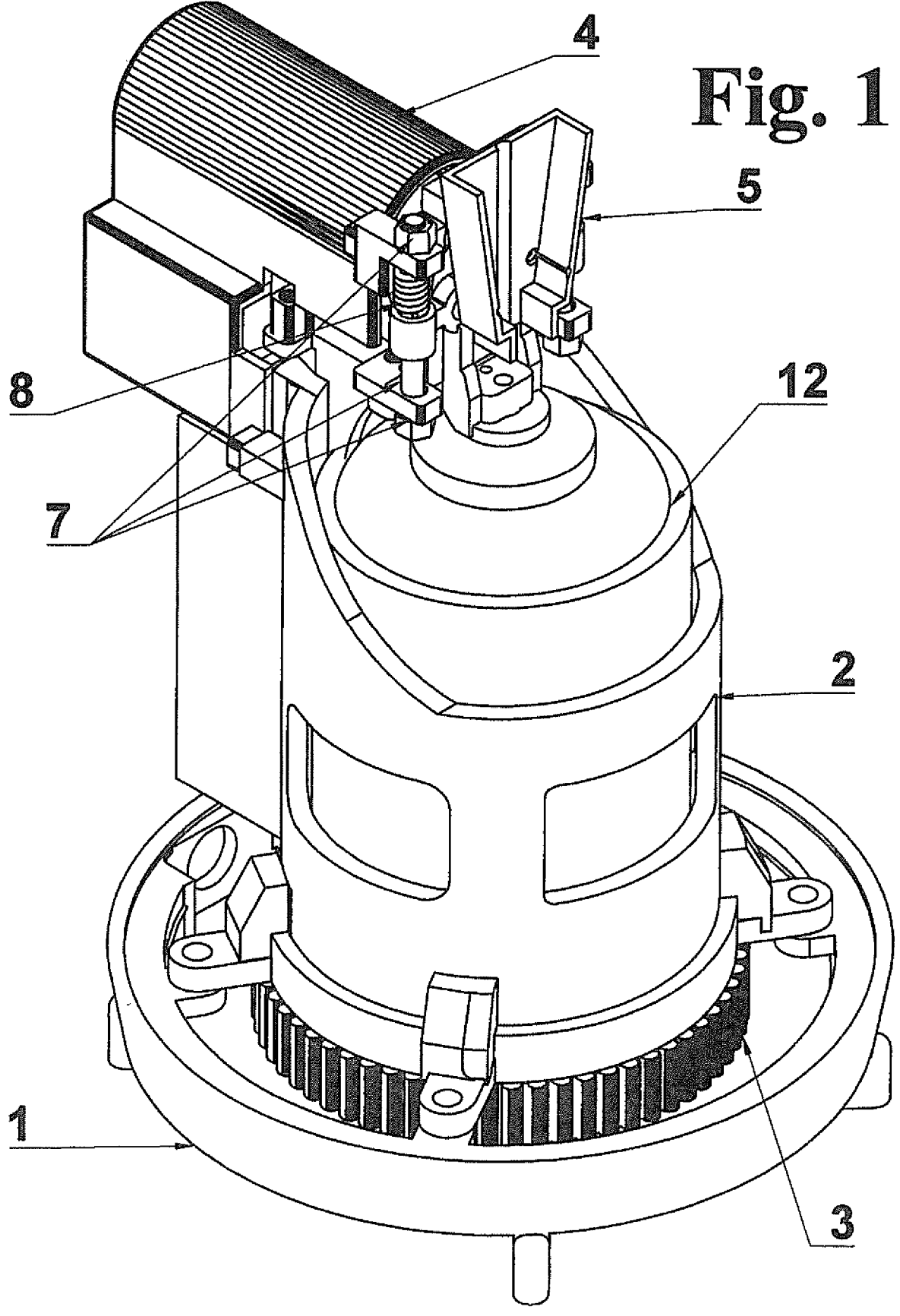
FIG. 1 is an isometric view of various components of the invention consisting of detail 1, the base; detail 2, the major connector; detail 3, the major connector screw cap; detail 4 the DC motor cover and PCB mount; detail 5, the spray shield; detail 7, the scotch yoke constraint pins and nuts; detail 8 the scotch yoke constraining pin springs; and detail 12, an illustration of an aerosol spray can.
Figure 2:
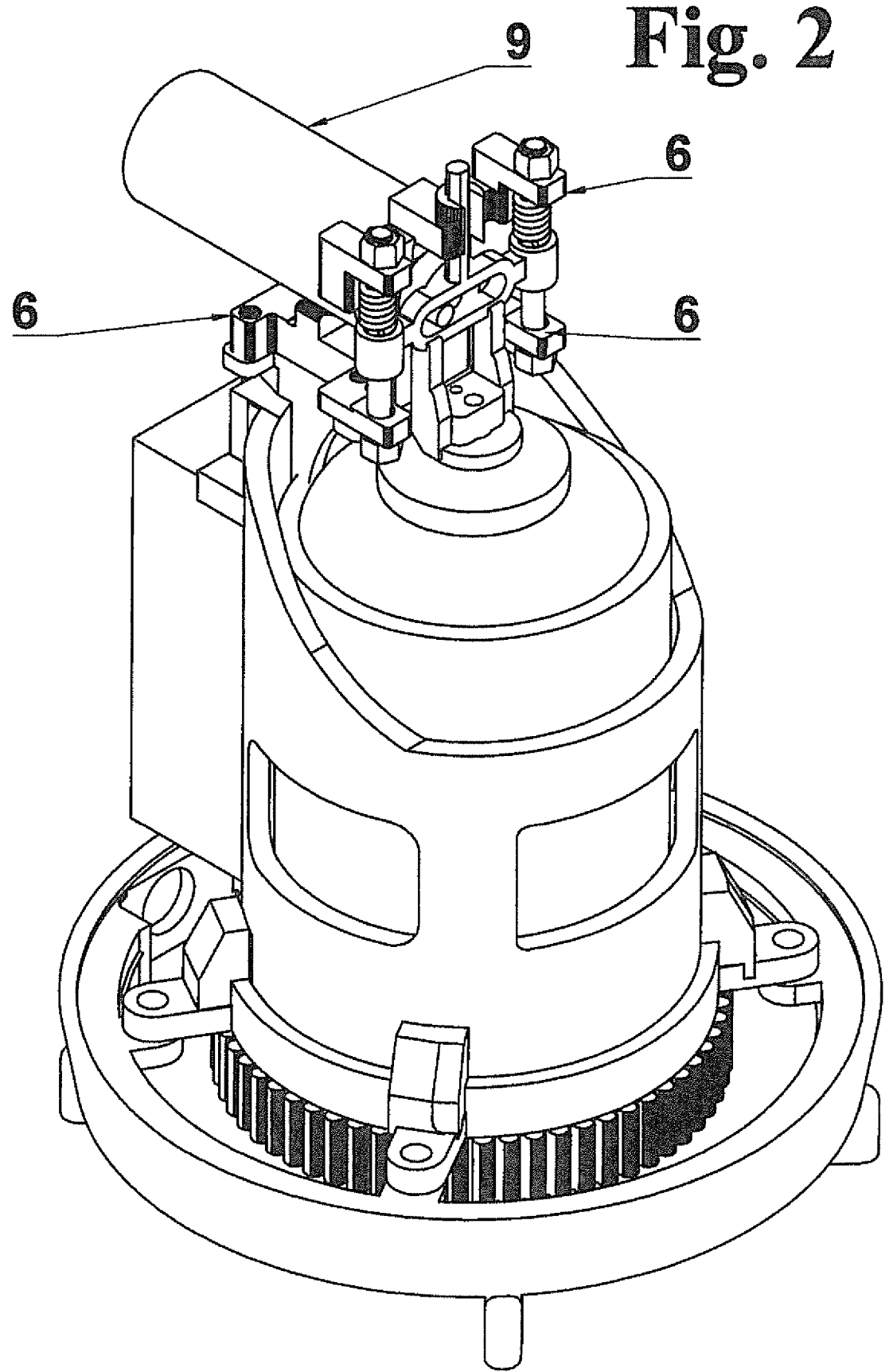
FIG. 2 depicts the assembly of parts including detail 9, the DC motor with the motor cover/PCB mount, detail 4, and spray shield, detail 5 removed.
Figure 3:
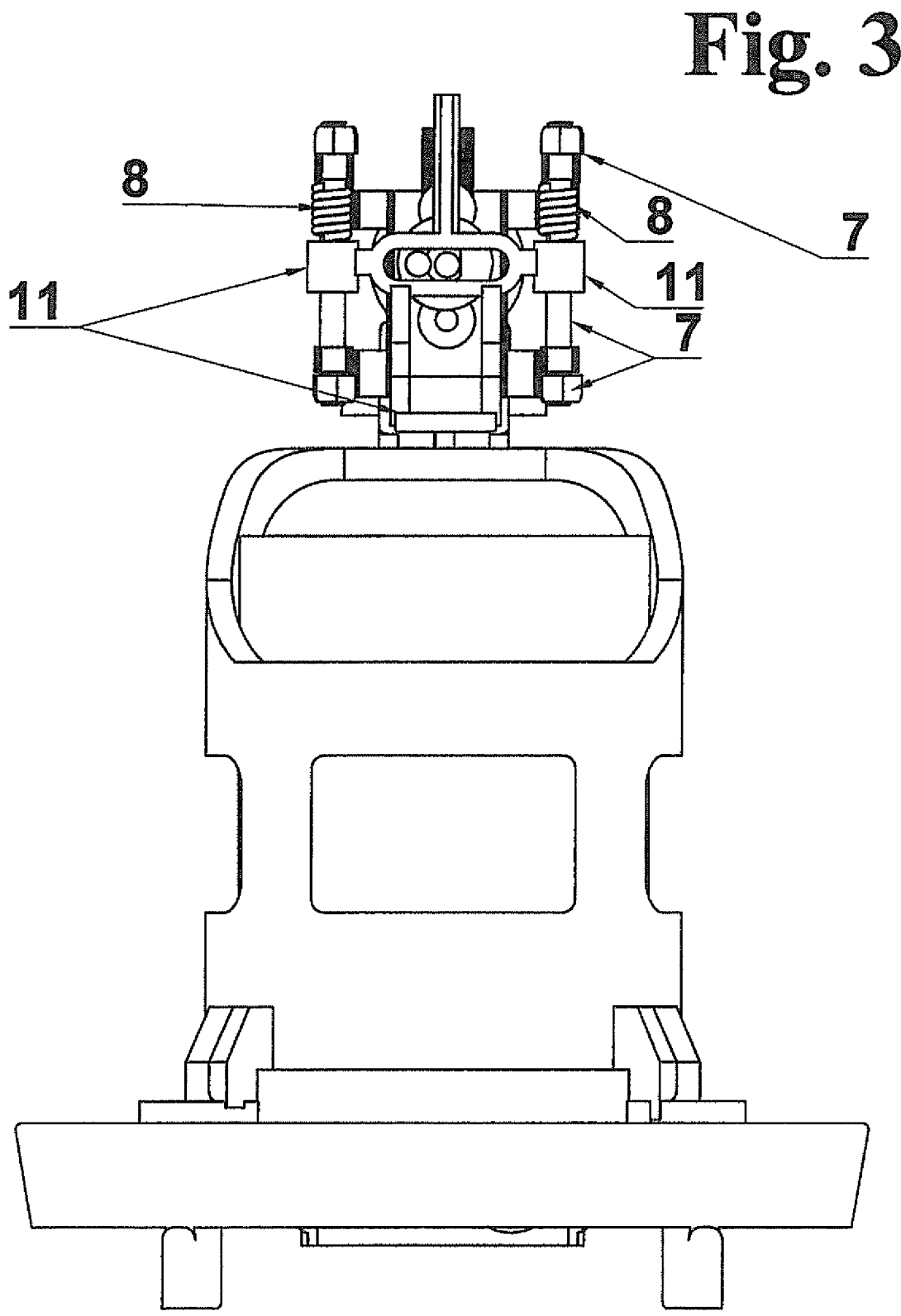
FIG. 3 depicts the modified scotch yoke, detail 11; the scotch yoke constraining pins and nuts, detail 7; and detail 8, the scotch yoke constraining pin springs.
Figure 4:
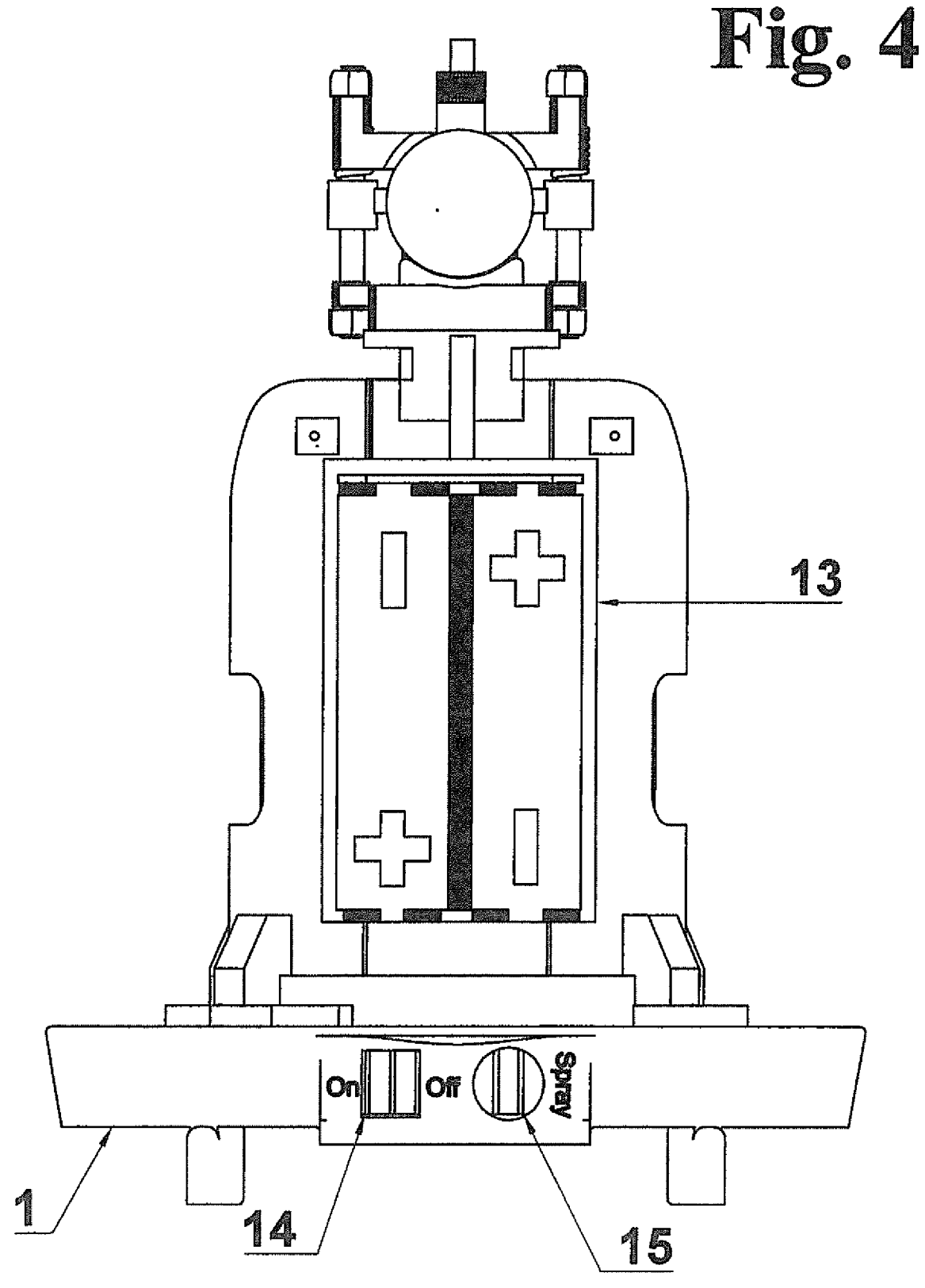
FIG. 4 shows the rear view of the device. Detail 13 is the battery holder; details 14 and are the mount holes, in the base detail 1, for the on/off switch and instant spray buttons respectively.
Figure 5:
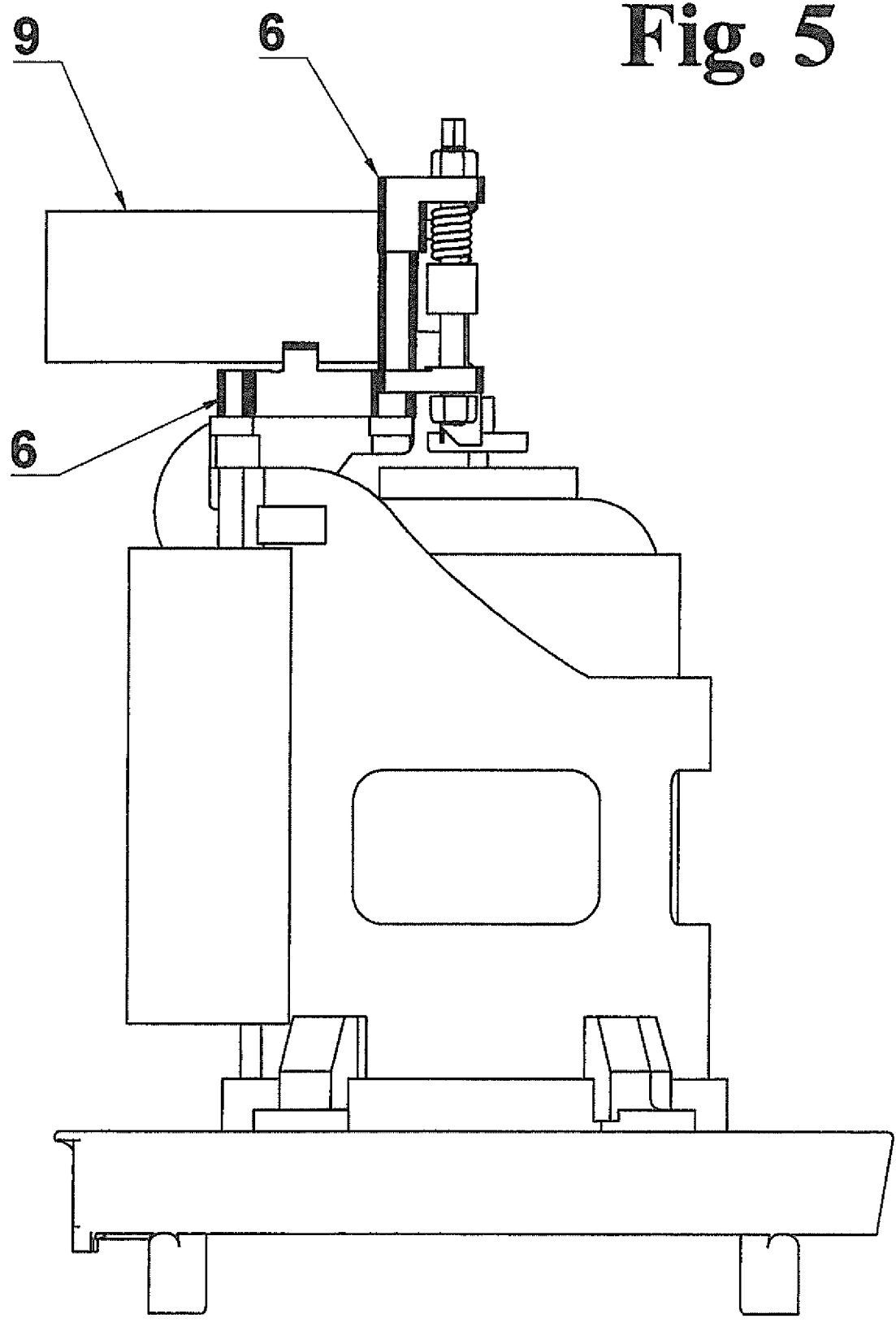
FIG. 5 depicts the device's side view. Detail 9 is a side view of the motor and detail 6 is a side view of the "modified scotch yoke mount/motor mount"
Figure 6:
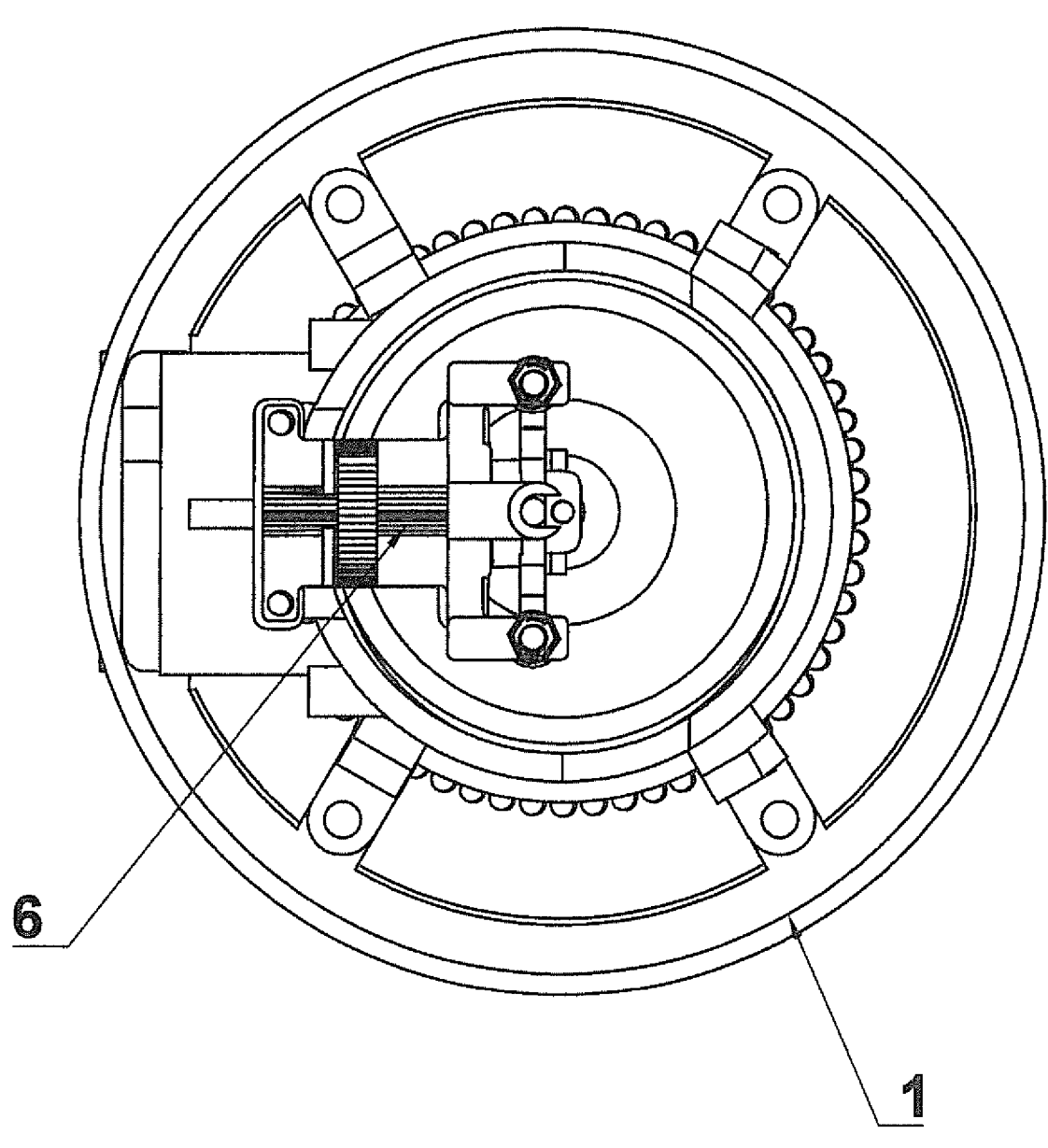
FIG. 6 shows the top view of the device. Detail 6 displays the top view of the "modified scotch yoke mount/motor mount". Detail 1 shows the top view of the base upon which the custom housing rests.
Figure 7:
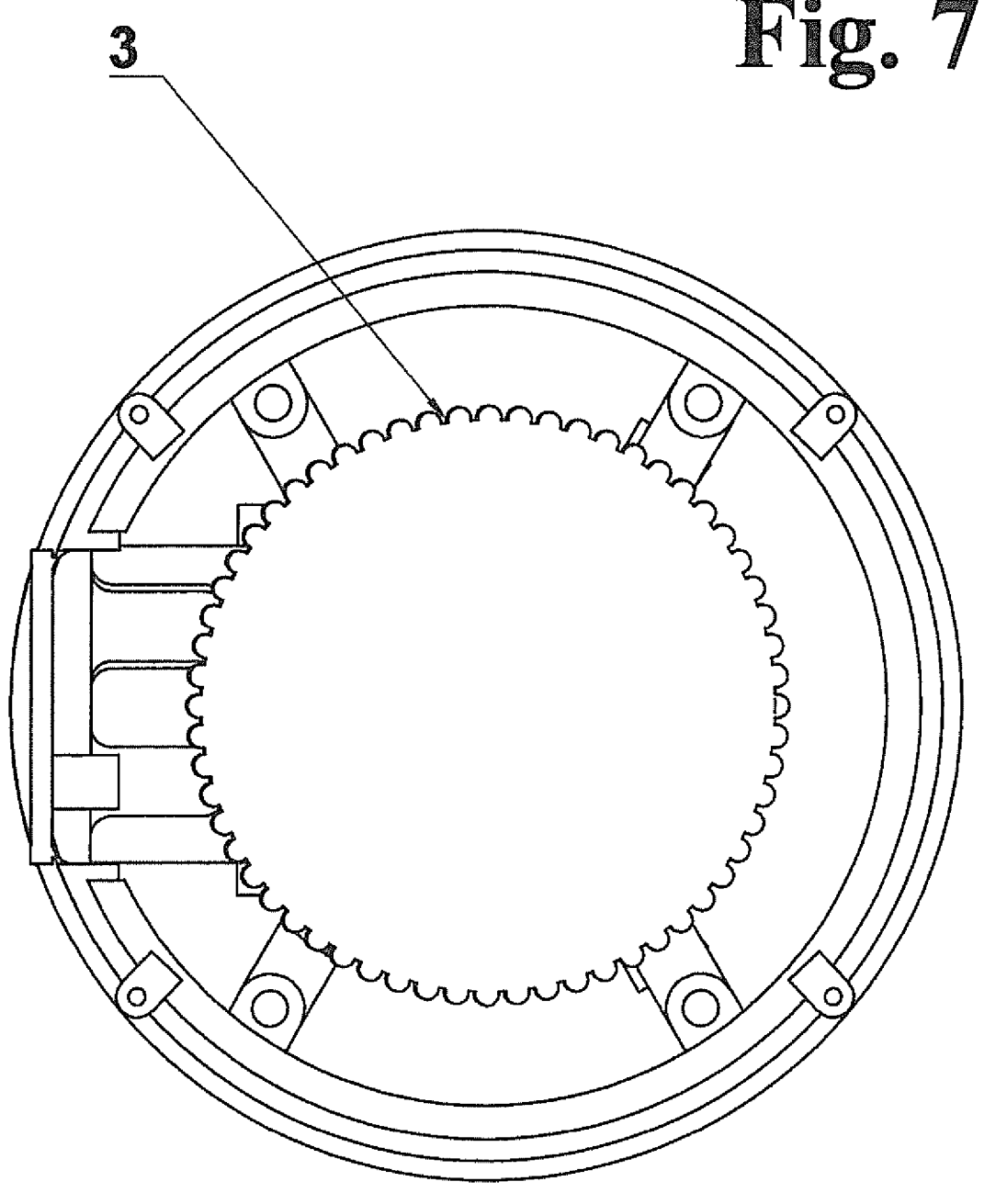
FIG. 7 shows the device's bottom view. Detail 3 is the bottom view of the major connector screw cap.
Figure 10:
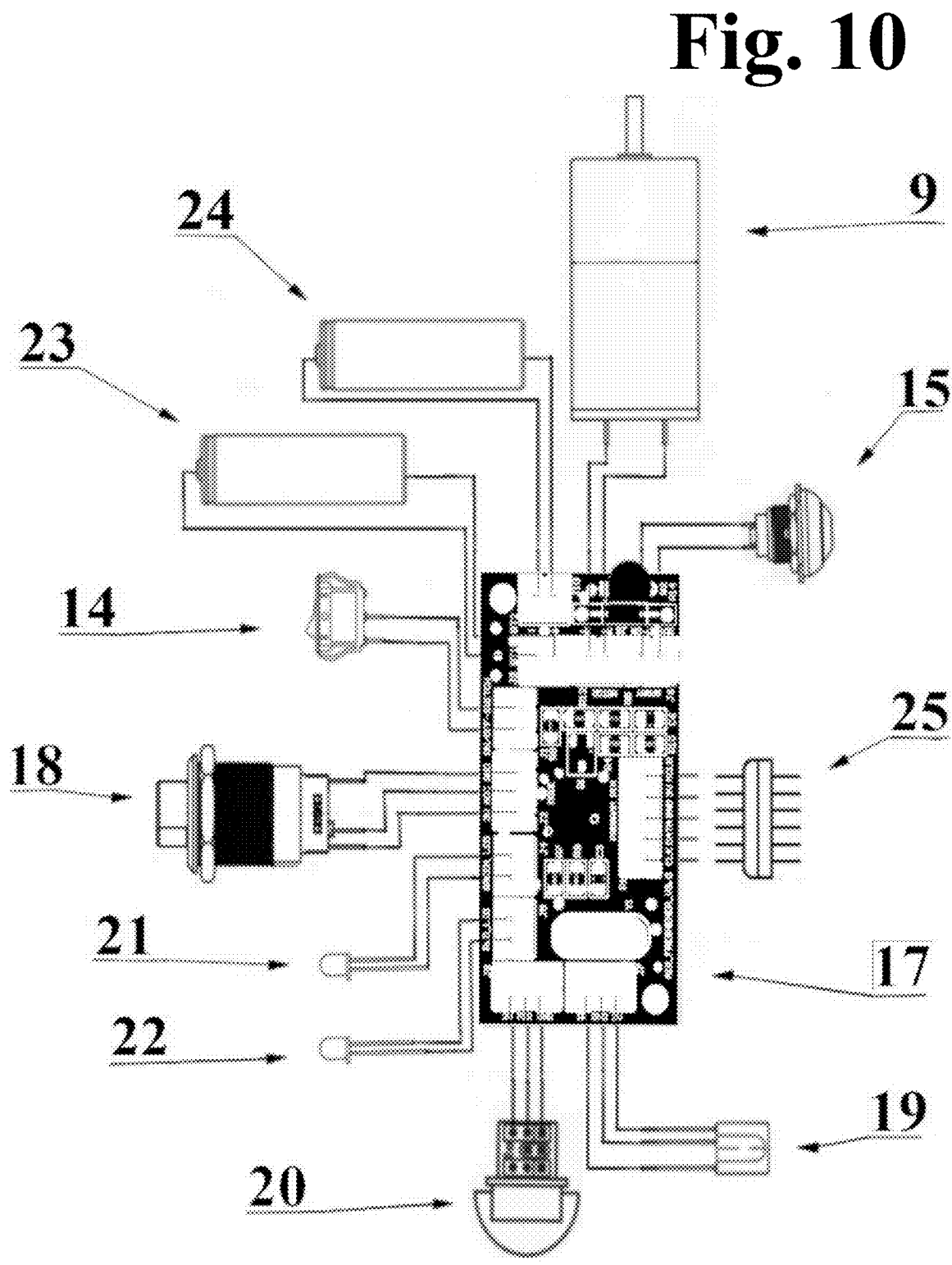
FIG. 10 is a schematic drawing depicting the pin outs for the electronic components of the printed circuit board, detail 17. Detail 14 is the on/off switch. Detail 15 depicts the instant spray button. Detail 18 depicts the rotary mode selector switch. The IR and PIR sensors are details 19 and 20 respectively. Details 21 and 22 depict the LED lights. Details 23 and 24 depict the batteries. Detail 25 is the programming plug. And detail 9 shows the dc motor.
Figure 11:
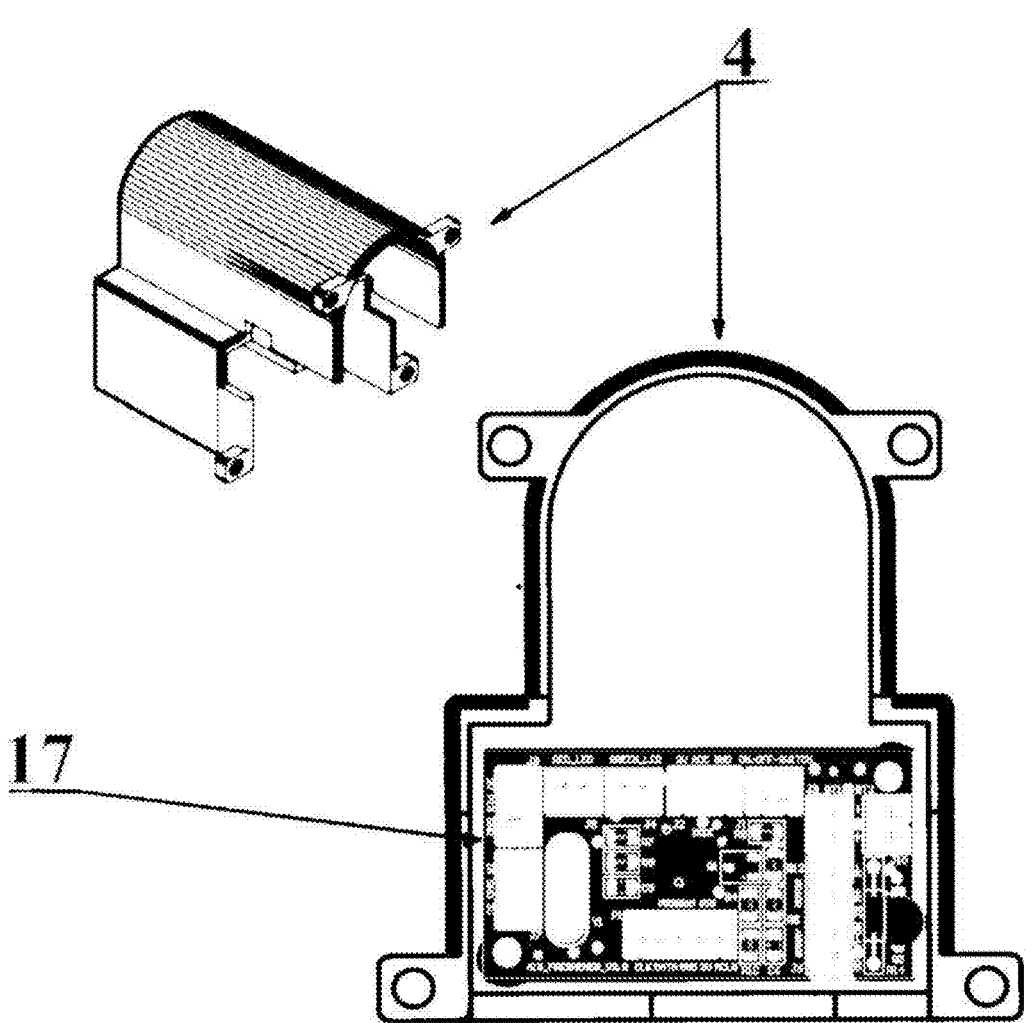
FIG. 11 shows the location of the printed circuit board, detail 17, inside the motor cover detail 4.
Figure 12:
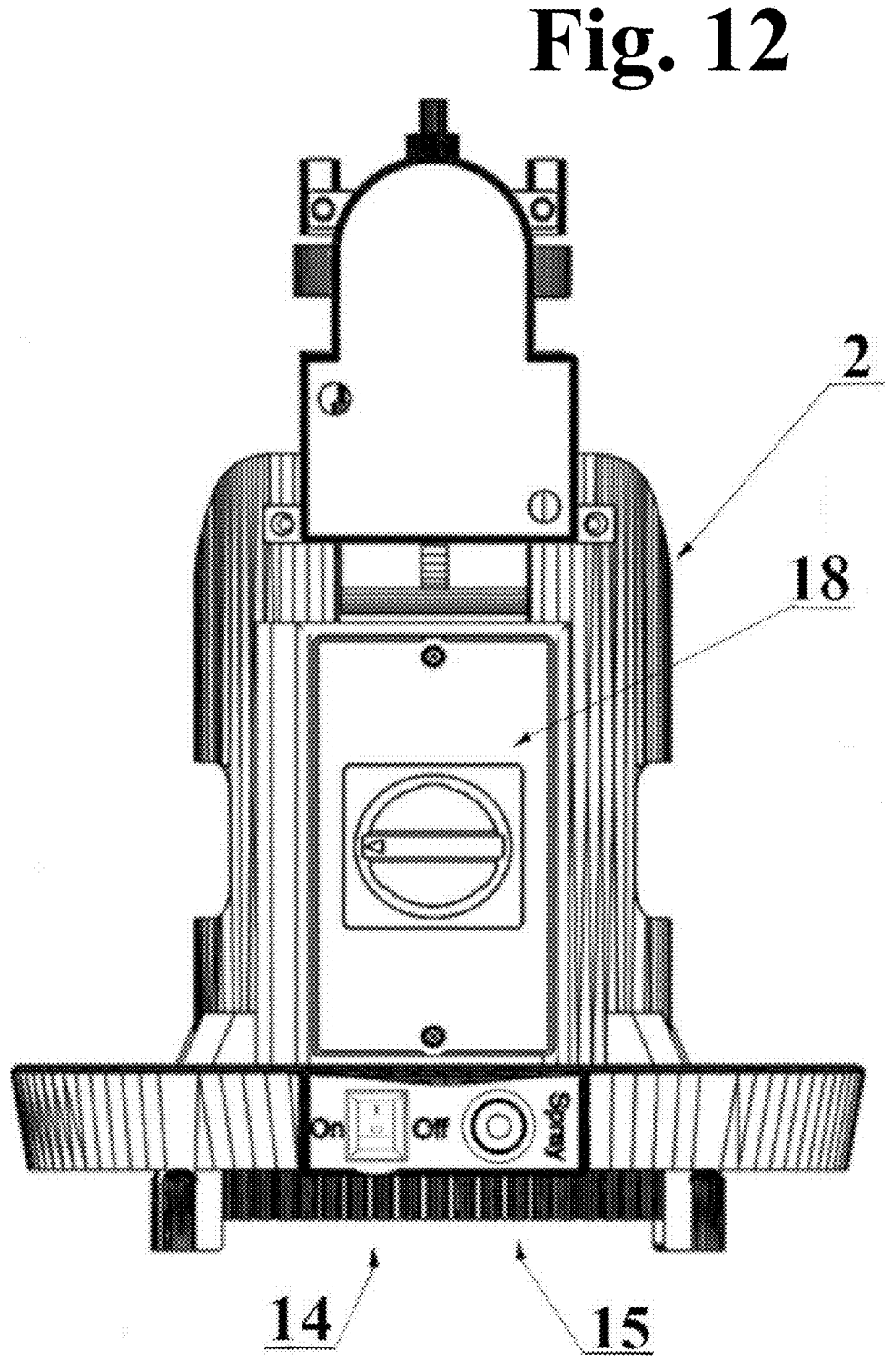
FIG. 12 is the back view of the major connector, detail 2, and the supporting base detail 1. The rotary switch detail 18 is mounted atop the battery holder, detail 13. The on/off switch and instant spray button, details 14 and 15 respectively, are mounted on the back of the devices base as shown in FIG. 12.
Figure 13:
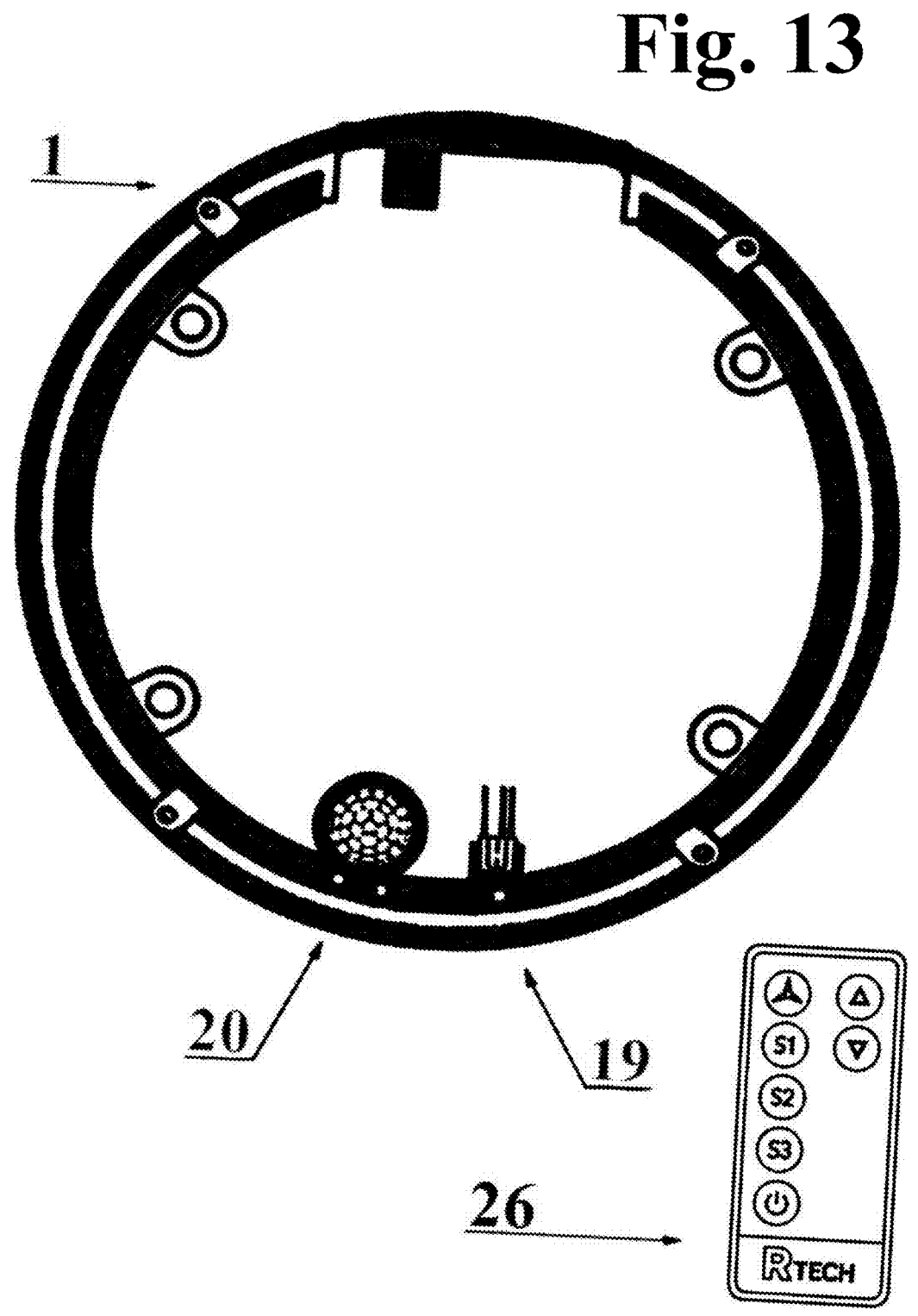
FIG. 13 depicts the mounting locations for the IR sensor, detail 19, and the PIR motion sensor, detail 20. Detail 26 represents the remote controller.

Power is derived from batteries mounted on the back of the major connector, details 2 and 13, FIG. 1 and FIG. 4. Motor control is provided by a PCB mounted inside the motor cover/PCB mount detail 4, FIGS. 1, 8, 11, and 12. The power on/off switch, detail 14, and instant spray button, detail 15, are mounted on the back of the base, detail 1. The device can be powered on by human motion detected by the PIR sensor, FIGS. 10 and 13, when the rotary mode selector switch, detail 18 FIGS. 10 and 12, is in the PIR sensor mode. The functions of the device can be controlled remotely via the remote controller, detail 26, signaling to the IR sensor detail 19 FIGS. 10 and 13.

The motor, detail 9, FIGS. 2, 5, 8 and 10, is mounted on the "modified scotch yoke mount/motor mount" detail 6 FIG. 8. The modified scotch yoke spindle detail 10 FIGS. 3 and 8 transforms rotational motion into linear force by way of exerting upward and downward pressure on the horizontal elliptical opening of the modified scotch yoke detail 11 FIGS. 3 and 8. The nozzle of the aerosol spray can is activated by the downward force of the modified scotch yoke, detail 10 FIGS. 3 and 8. The air is treated through a spray of a liquid mixture from the aerosol spray can detail 12, FIGS. 1 and 8.

The major connector detail 2, FIGS. 1 and 8, holds the aerosol spray can detail 12. Once the custom housing (detail 16) is removed, the air treatment machine can be lifted and the major connector screw cap removed. Then the aerosol spray can, detail 12, will be free to slide out from the bottom of the major bracket, detail 2, for removal and replacement when empty.

The invention claimed is:

1. An air-treatment machine comprising: a base dimensioned to receive a removable decorative housing; a major bracket attached to the base, wherein the base supports the major bracket, an on/off switch, an instant spray button, a passive infrared (PIR) motion sensor, and an infrared (IR) remote sensor; the major bracket configured to secure a spray can via a screw cap, the major bracket further supporting a rotary motor mount, a rotary motor, a mode selector switch, batteries for power supply, and a circuit board configured to control functional operations including actuation of the rotary motor and coordination of electronic components; the rotary motor mount attached to the major bracket; the rotary motor mounted onto the rotary motor mount; a modified scotch yoke mechanism connected to the rotary motor, wherein the scotch yoke mechanism comprises a pair of springs and guide pins functioning with a circular motor spindle to deliver precise downward force to actuate a spray can nozzle, thereby enabling the air-treatment machine to emit a controlled spray of air-treatment fluid through the spray can nozzle.

* * * * *